(12) United States Patent
Durand et al.

(10) Patent No.: US 8,340,770 B2
(45) Date of Patent: Dec. 25, 2012

(54) CONTROLLING SEIZURE ACTIVITY WITH ELECTRICAL STIMULATION

(76) Inventors: Dominique M. Durand, Solon, OH (US); David Yuang Tang, Bratenahl, OH (US); Alicia L. Jensen, Cleveland, OH (US)

(*) Notice: Subject to any disclaimer, the term of this patent is extended or adjusted under 35 U.S.C. 154(b) by 1217 days.

(21) Appl. No.: 12/215,387

(22) Filed: Jun. 26, 2008

(65) Prior Publication Data

US 2009/0030480 A1  Jan. 29, 2009

Related U.S. Application Data

(60) Provisional application No. 60/946,179, filed on Jun. 26, 2007.

(51) Int. Cl.
*A61N 1/00* (2006.01)
(52) U.S. Cl. ........................................... 607/45
(58) Field of Classification Search .................. None
See application file for complete search history.

(56) References Cited

U.S. PATENT DOCUMENTS

| 2003/0100539 A1* | 5/2003 | Bear et al. ................ 514/150 |
| 2007/0067003 A1* | 3/2007 | Sanchez et al. ............ 607/45 |
| 2007/0213786 A1* | 9/2007 | Sackellares et al. ........ 607/45 |

FOREIGN PATENT DOCUMENTS

WO   WO 2004/037342 A2   5/2004

* cited by examiner

*Primary Examiner* — Christopher D Koharski
*Assistant Examiner* — Elizabeth K So

(57) ABSTRACT

Apparatus and methods associated with controlling seizure activity with electrical stimulation that either suppress axonal conduction between brain structures and/or that generate a desired response in a targeted neuronal pool are described. One example apparatus includes an implantable stimulating electrode that provides an electrical stimulus to fiber tracts of the hippocampal commissure of the brain of a subject. The stimulus may be a high frequency structure that prevents communication of signals associated with an epileptic episode and/or prevents seizure activity in a target nucleus. The example apparatus may also include a detection logic that detects specific electrical activity in the central nervous system that identifies that an epileptic episode is imminent. The example apparatus includes a pacing system to selectively configure and apply the electrical stimulus to fiber tracts of the hippocampal commissure of the brain.

14 Claims, 5 Drawing Sheets

CONTROLLING SEIZURE ACTIVITY WITH ELECTRICAL STIMULATION

CROSS REFERENCE TO RELATED APPLICATIONS

This application claims the benefit of U.S. Provisional Application 60/946,179 filed Jun. 26, 2007.

FEDERAL FUNDING NOTICE

The invention was developed with federal funding supplied under Federal Grant No. NS40785 provided by National Institute of Health. The Federal government has certain rights in the invention.

BACKGROUND

Neurological disorders (e.g., epilepsy) generally are characterized by abnormal neural activity. The abnormal neural activity may include, for example, abnormal electrical activity in the brain. Abnormal neural activity includes neural firing leading to unwanted symptoms, (e.g., seizure, parathesia). Neurological disorders typically are treated with drug therapy and surgery. However, accurately and safely delivering drugs into the nervous system, particularly the brain, can be difficult. Moreover, some drugs may cause unpleasant side effects that may be irreversible.

Surgical procedures are typically irreversible. Surgery to the brain has a high risk of complications. One of the current surgical methods includes severing the corpus callosum. This is known as a callossomy. By severing this axonal pathway, the neurosurgeon separates the two hemispheres of the brain, and reduces recurrent, abnormal activity (e.g. epileptic seizures). This solution permanently damages electrical communication through that pathway and carries the risks of all highly invasive surgical procedures to the brain.

Electrical stimulation is an emerging therapy for treating neurological disorders such as epilepsy. Electrical stimulation for seizure suppression has conventionally been unsuccessful due, at least in part, to the lack of effective targets and inadequate stimulation parameters. Conventional approaches have suffered because the mechanisms of action for electrical stimulation have been unknown. Conventional electrical stimulation has traditionally targeted areas located near the stimulating electrode. For example, conventional clinical application of electrical stimulation has focused upon the placement of electrodes within cellular nuclei in the brain rather than in or near the axonal fiber tracts. However, by limiting the stimulation to the area around the stimulating electrode (e.g. cellular nuclei), the treated area is limited. Because the abnormal electrical activity can affect large areas of the brain simultaneously, targeting only areas located near the stimulating electrode limits the effectiveness of the treatment. Thus, other conventional approaches (e.g., WO 2004/037342) have used implanted electrodes to stimulate "white matter" (e.g., fiber tract) to stimulate and "electrically overdrive" epileptogenic structures.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
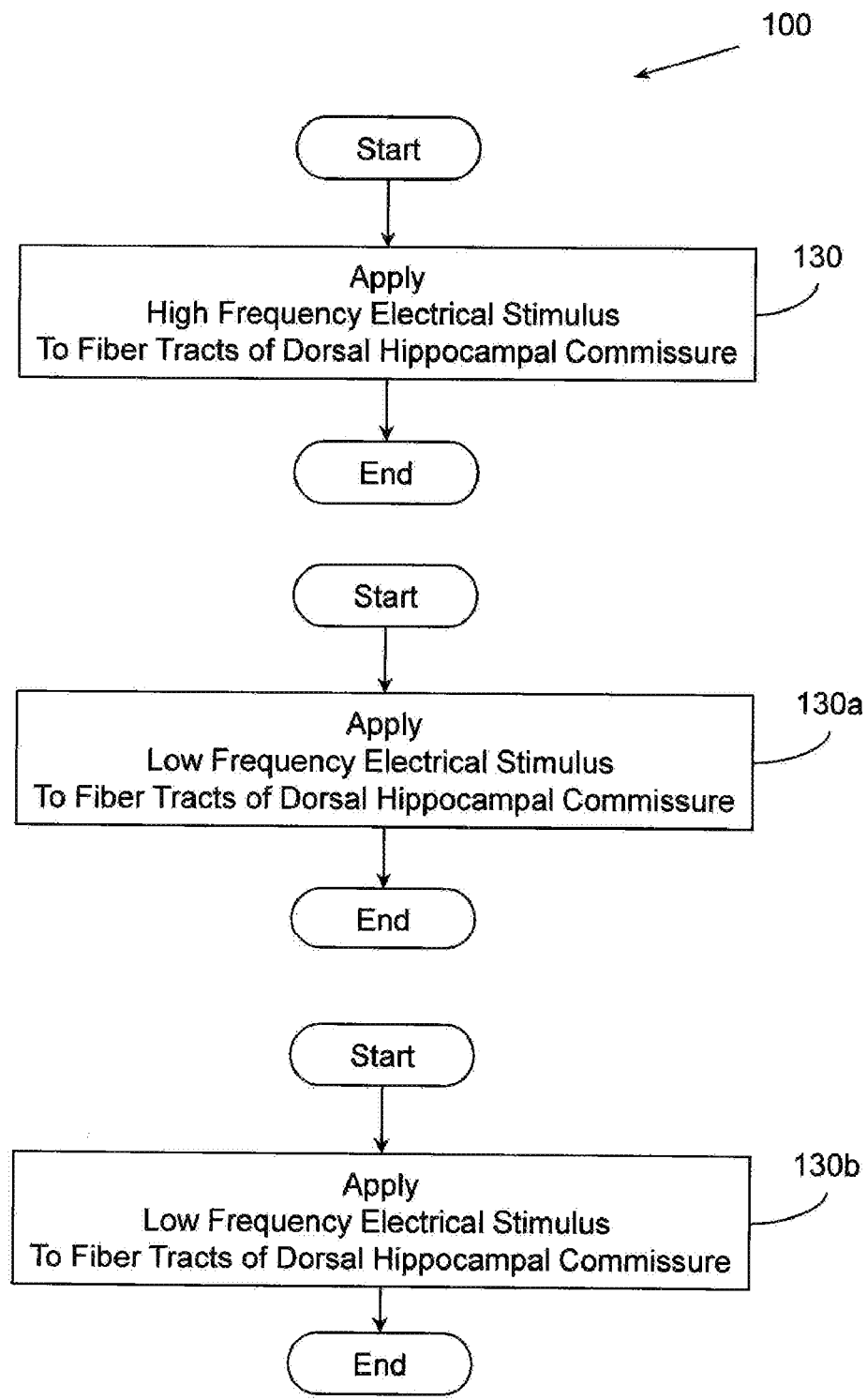
FIG. 1 illustrates an example method associated with controlling seizure activity with electrical stimulation.

Electrical stimulation can suppress neuronal activity with appropriate waveforms and targets. Rather than target specific small locations in gray matter, and rather than "electrically overdriving" epileptogenic regions, example systems and methods target a fiber bundle that affects a large portion of the brain. Targeting the fiber bundle facilitates suppressing axonal conduction between structures and/or facilitates generating a desired response in a target neuronal pool associated with the fiber bundle. Targeting the fiber bundle facilitates preventing the propagation of epileptic seizures outside of the epileptic focus.

Electrically treating epileptic episodes may include analysis of the electrical activity in the brain to detect the onset of abnormal electrical activity and to generate specific treatment waveforms based on the detected abnormal electrical activity. The specific treatment waveforms may include one or a combination of continuous and periodic responsive electrical stimulation to the axonal fiber tracts between the hippocampi. The method may include stimulating the fiber tracts with low frequency stimulus, high frequency stimulus, or a combination of both low and high frequency stimulus. The electrical stimulus does not "overdrive" gray matter associated with the fiber tracts as described in conventional systems but rather suppresses axonal conduction between structures (e.g., two sides of hippocampus) and/or generates a desired response (e.g., synchronization, inhibitory response, synaptic depression) in a targeted neuronal pool.

A stimulating electrode may be placed within or directly adjacent to the axonal fiber tracts of the hippocampus to provide the electrical stimulus. A pacing system may control the electrical stimulus applied by the stimulating electrode. The stimulating electrode and its associated lead wires that connect the pacing system to the stimulating electrode may both be subcutaneous. A detection logic that may use subcutaneous sensors may detect and diagnose specific electrical activity and communicate with the pacing system. The pacing system may also determine the electrical stimulation to apply based, at least in part, on the determination made by the detection logic. The electrical stimulation may reduce, alleviate, or prevent an epileptic episode by suppressing axonal conduction between structures (e.g., hippocampi) and/or by producing a desired response (e.g., synchronization, inhibitory response) in a targeted neuronal pool. The waveform of the electrical stimulus applied may therefore depend upon what is detected by the detection logic. In one example, the electrical stimulus may be applied as treatment before abnormal electoral stimulus is detected.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer component", as used herein, refers to a computer-related entity (e.g., hardware, firmware, software in execution, combinations thereof). Computer components may include, for example, a process running on a processor, a processor, an object, an executable, a thread of execution, and a computer. A computer component(s) may reside within a process and/or thread. A computer component may be localized on one computer and/or may be distributed between multiple computers.

"Data store", as used herein, refers to a physical and/or logical entity that can store data. A data store may be, for example, a database, a table, a file, a data structure (e.g. a list, a queue, a heap, a tree) a memory, a register, and so on. In different examples, a data store may reside in one logical and/or physical entity and/or may be distributed between two or more logical and/or physical entities.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"Signal", as used herein, includes but is not limited to, electrical signals, optical signals, analog signals, digital signals, data, computer instructions, processor instructions, messages, a bit, a bit stream, and so on, that can be received, transmitted and/or detected.

"Software", as used herein, includes but is not limited to, one or more executable instruction that cause a computer, processor, or other electronic device to perform functions, actions and/or behave in a desired manner. "Software" does not refer to stored instructions being claimed as stored instructions per se (e.g., a program listing). The instructions may be embodied in various forms including routines, algorithms, modules, methods, threads, and/or programs including separate applications or code from dynamically linked libraries.

Example methods may be better appreciated with reference to flow diagrams. For purposes of simplicity of explanation, the illustrated methodologies are shown and described as a series of blocks. However, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates a method 100 associated with controlling seizure activity with electrical stimulation. Method 100 includes, at 130, applying electrical stimulus to suppress axonal conduction between structures connected by the axon fiber tract to which the electrical stimulus is applied and/or to generate a desired response in a targeted neuronal pool associated with the axon fiber tract. The electrical stimulus may be applied, for example, to fiber tracts of the hippocampal commissure of the brain of a subject. The electrical stimulus may be applied via an implanted stimulating electrode. In one example the electrical stimulus may be provided in response to the detecting of specific electrical activity that identifies that an epileptic episode is imminent. The electrical stimulus may be configured with respect to, for example, frequency, duration, continuity, intensity, and/or shape (e.g., sinusoidal, triangular) based on the detected electrical activity. For example, detected electrical activity that indicates that a grand mal seizure is imminent may lead to a first electrical stimulus having a first set of properties while detected electrical activity that indicates that a petite mal seizure is imminent may lead to a second electrical stimulus having a second, different, set of properties.

The electrical stimulus applied at 130 may be a high frequency electrical stimulus to alleviate the epileptic episode by suppressing axonal conduction between brain structures and/or regions. The stimulus may alleviate the epileptic episode by suppressing propagation of epileptic episode electrical activity through fiber tracts of the hippocampal commissure. This suppression may prevent the communication of signals of the epileptic episode. The fiber tracts of the hippocampal commissure to which the electrical stimulus may be applied include the dorsal and/or ventral hippocampal commissure. The high frequency electrical stimulus may be of a sinusoidal shape and may have a frequency between 80 Hertz and 300 Hertz. The high frequency electrical stimulus may be delivered with a current in the range of 100 micro-amps to 5 milli-amps. In another example the high frequency electrical stimulus may be delivered as a series of pulses. The pulses may have, for example, a pulse width of 50 micro-seconds to 1 milli-second and may be delivered with a current in the range of 100 micro-amps to 5 milli-amps. One skilled in the art will understand that other waveforms, frequencies, and currents may be employed. In one example, the high frequency electrical stimulus may also be periodically applied in response to the detected specific electrical activity in the central nervous system. For example, the specific electrical activity may identify that an epileptic episode is imminent. Periodic application of the high frequency electrical stimulus may prevent the epileptic episode.

In another example, the electrical stimulus applied at 130 may be a low frequency electrical stimulus that generates a desired response in a targeted neuronal pool associated with the fiber tract of the hippocampal commissure. The desired response may be, for example, generating a synchronization between neurons in the targeted neuronal pool producing an inhibitory response or synaptic depression in the targeted neuronal pool. The low frequency electrical stimulus may have a frequency between 0.1 Hertz and 10 Hertz. One skilled in the art will understand that other frequencies may also be used. The electrical stimulus may minimize the epileptic episode and in some examples may even prevent the epileptic episode before it is detected. The low frequency electrical stimulus may be applied periodically, intermittently, and/or continuously based, in one example, on detected electrical activity.

In one example, the electrical stimulus applied at 130 may include both high and low frequency components. The high frequency portion may selectively suppress axonal conduction in the fiber tracts of the hippocampal commissure and the low frequency portion may produce a response in a target neuronal pool associated with the fiber tracts of the hippocampal commissure. In one example, the electrical stimulus may be provided as a low frequency series of high frequency waveforms. One skilled in the art will appreciate that various combinations of high frequency and low frequency electrical stimulations may be employed to both suppress axonal conduction and to generate a desired response in a targeted neuronal region.

In one example, the electrical stimulus is provided by the same electrode that monitors electrical activity in the central nervous system of the subject. Thus, the electrode may be used for both stimulating and sensing. The electrical stimulus may be applied to the dorsal hippocampal commissure and/or the ventral hippocampal commissure.

Figure 2:
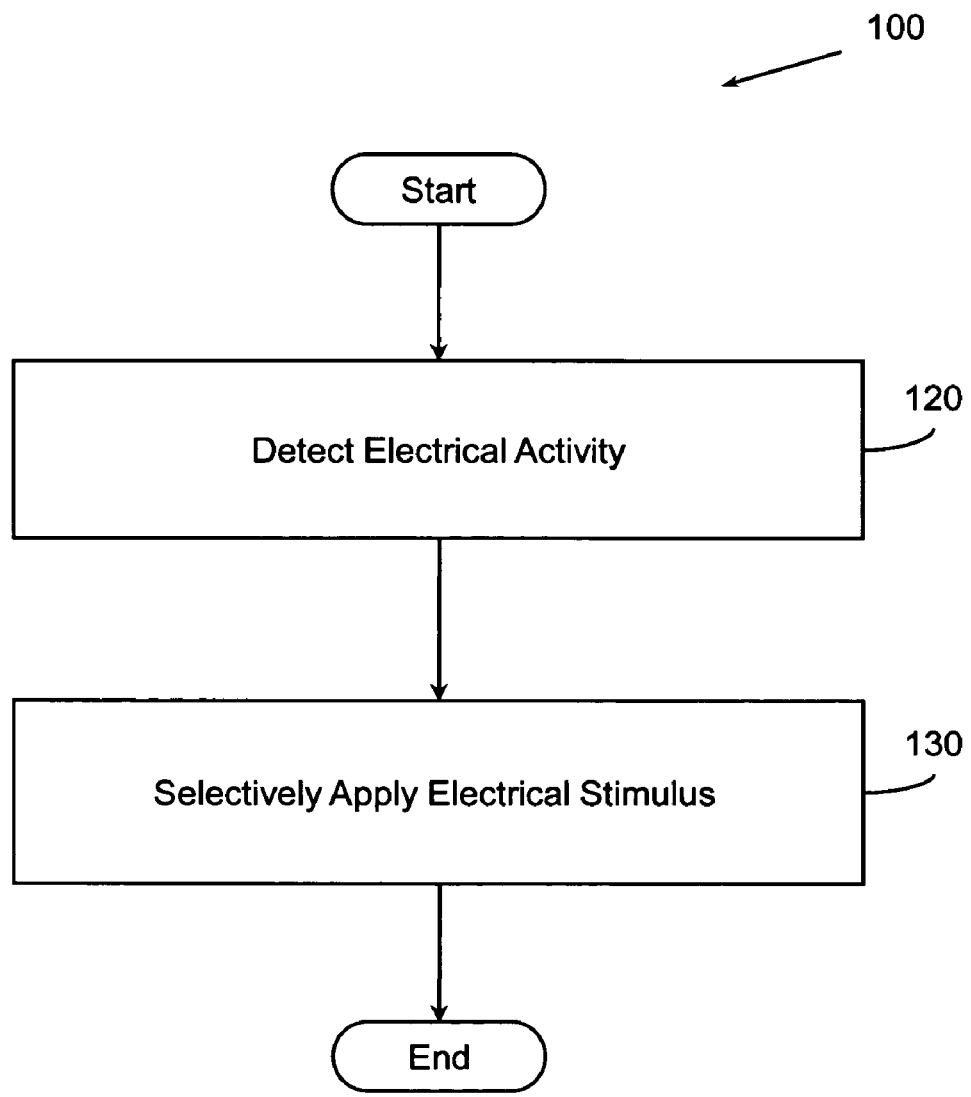
FIG. 2 illustrates an example method associated with controlling seizure activity with electrical stimulation.

FIG. 2 illustrates another embodiment of method 100. In this embodiment, method 100 includes, at 120, detecting specific electrical activity in the central nervous system of a subject in which a sensor is implanted. The specific electrical activity may identify that an epileptic episode is imminent. The detection may be performed with sensors and a computer component that analyzes data and/or signals from the sensors. The computer component may use a data store to store the signals from the sensors to analyze time periods of sensor readings. The specific electrical activity may be analyzed to determine a property of an electrical stimulus to be applied in response to detecting the abnormal electrical activity.

While FIG. 2 illustrates various actions occurring in serial, it is to be appreciated that various actions illustrated in FIG. 2 could occur substantially in parallel. By way of illustration, a first process could detect specific electrical activity and a second process could selectively apply an electrical stimulus to fiber tracts. While two processes are described, it is to be appreciated that a greater and/or lesser number of processes could be employed and that lightweight processes, regular processes, threads, and other approaches could be employed.

Figure 3:
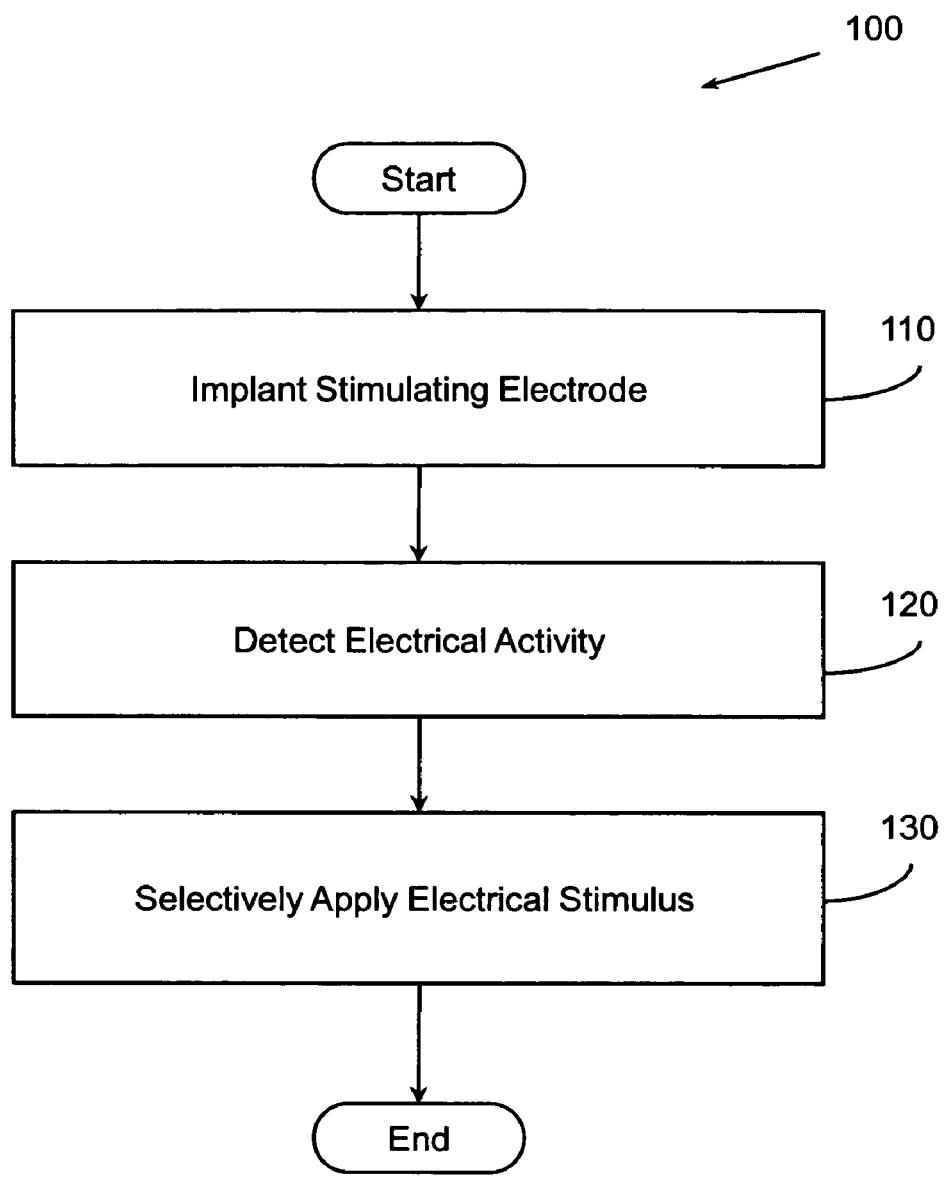
FIG. 3 illustrates an example method associated with controlling seizure activity with electrical stimulation.

FIG. 3 illustrates another embodiment of method 100. This embodiment includes, at 110, implanting a stimulating electrode. The implantation of the stimulating electrode may be performed by surgery. The stimulating electrode may be connected to and/or form a part of an apparatus like that described in connection with FIG. 3 and FIG. 4.

Figure 4:
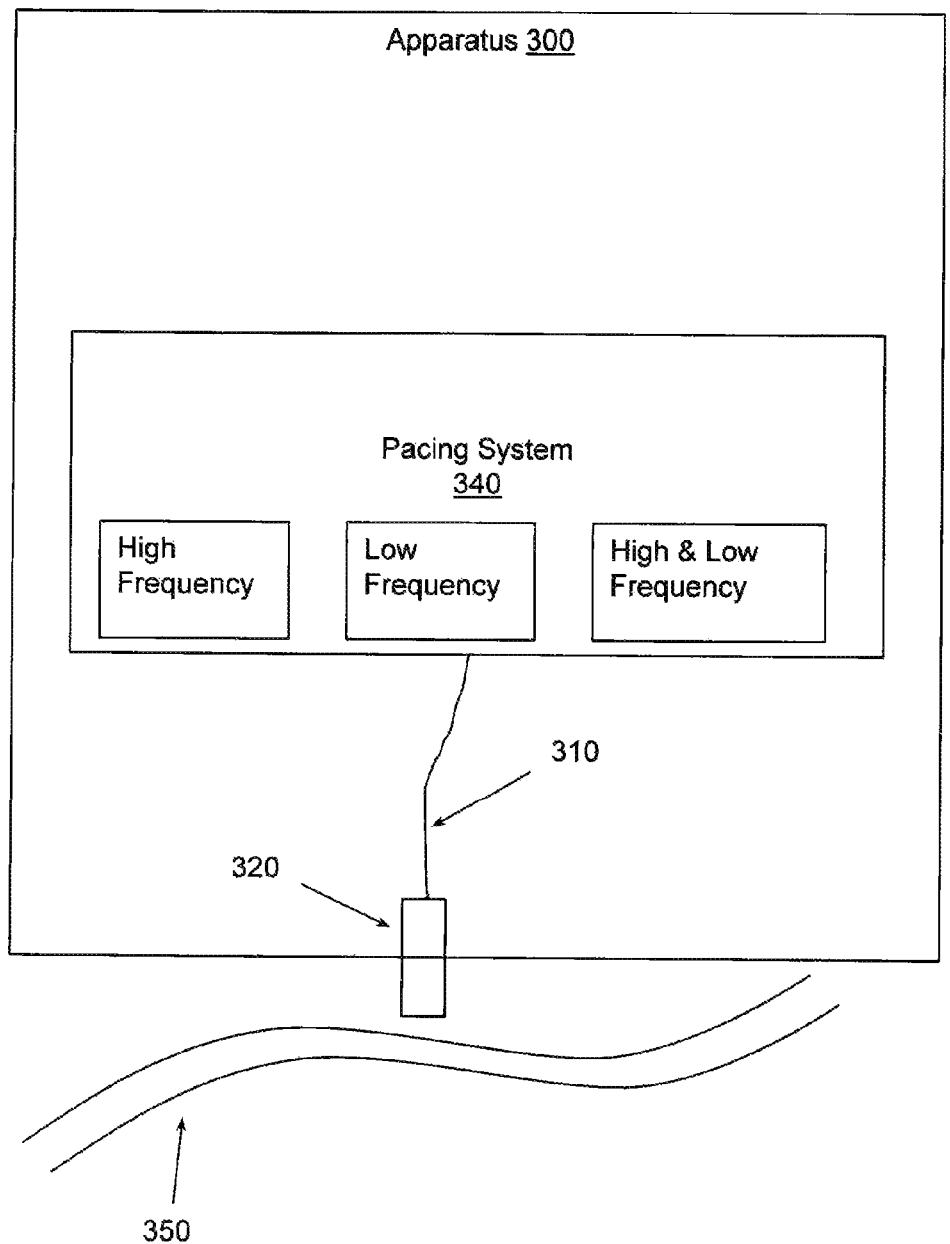
FIG. 4 illustrates an example system associated with controlling seizure activity with electrical stimulation.

FIG. 4 illustrates an apparatus 300 that controls seizure activity with electrical stimulation. In one example apparatus 300 controls seizure activity by suppressing axonal conduction between brain structures and/or regions. In another example, apparatus 300 controls seizure activity by generating a desired response in a targeted neuronal region. Apparatus 300 includes a lead wire 310 that is configured to carry an electrical signal or electrical stimulus. In one example, the lead wire 310 includes a single conductor, in which case two separate lead wires would be used to complete a circuit. In another example, a plurality of conductors may be included in the lead wire 310 allowing for completion of the circuit with one lead wire 310. Additionally, the lead wire 310 may be shielded to prevent electrical interference.

Apparatus 300 may also include an implantable stimulating electrode 320 that provides an electrical stimulus to fiber tracts of the hippocampal commissure 350 of the brain of the subject. The stimulating electrode may be surgically implanted. The procedure of implanting the electrode may be less invasive to the brain than traditional surgical methods of severing the corpus callosum, which is referred to as a callossomy. Implantation of the stimulating electrode is unlike a callossomy because it does not permanently sever electrical communication through that pathway of the brain. Rather than permanently physically isolating structures that are connected by the corpus callosum, apparatus 300 may selectively, configurably, temporarily, and reversibly "sever" electrical communications through the pathway. This facilitates halting the spread of signals associated with an epileptic episode, which may confine the episode to its foci and thereby mitigate the severity of the episode. For example, by electrically blocking this pathway signals may be prevented from passing from one side of the hippocampus to the other side of the hippocampus.

Apparatus 300 includes a pacing system 340 to selectively apply the electrical stimulus to fiber tracts of the hippocampal commissure 350 of the brain of the subject to alleviate an epileptic episode. When a high frequency electrical stimulus is applied, the apparatus 300 may suppress axonal conduction between structures and/or regions associated with the fiber tracts. The electrical stimulus may be applied via the implantable stimulating electrode 320. The implantable stimulating electrode 320 is attached to the pacing system 340 by the lead wire 310. The pacing system 340 may be associated with selectively applying electrical stimulus.

In one example, the electrical stimulus is a high frequency electrical stimulus that may have a frequency between 80 Hertz and 300 Hertz. The high frequency electrical stimulus may take forms including, for example, a sinusoidal wave, a pulse train, and so on. The high frequency electrical stimulus may be delivered with a current of between 100 micro-amps and 5 milli-amps. One skilled in the art will understand that other frequencies, waveforms, and currents may be employed. The stimulus may alleviate the epileptic episode by suppressing propagation of epileptic episode electrical activity within fiber tracts of the hippocampal commissure. This suppression may prevent the communication of signals of the epileptic episode. Furthermore, the high frequency electrical stimulus may be used to alleviate the epileptic episode after detection of the specific electrical activity.

In another example, the electrical stimulus is a low frequency electrical stimulus that modifies the epileptic episode by generating a desired response in a targeted neuronal region associated with the hippocampal commissure. The desired response may include, for example, synchronizing neurons in the targeted neuronal region and/or generating an inhibitory response in the targeted neuronal region. The low frequency electrical stimulus may have a frequency between 0.1 Hertz and 10 Hertz. One skilled in the art will understand that other frequencies may also be used. In one example, the electrical stimulus minimizes the frequency of the epileptic episodes and may be applied continuously. The low frequency electrical stimulus may be used to prevent specific electrical activity (e.g. epileptic episodes) before an episode is detected. For example, the electrical stimulus could be provided continuously or at regular intervals to prevent an episode before symptoms (e.g. abnormal electrical activity that precedes an epileptic seizure) are detected. The electrical stimulus may also prevent the epileptic episode before it is detected. The electrical stimulus may be applied periodically, intermittently, and continuously.

In one example, the electrical stimulus may be applied to the dorsal hippocampal commissure while in another example the electrical stimulus may be applied to the ventral hippocampal commissure. In another example, the stimulating electrode 320 may be an implanted stimulating electrode that is placed directly adjacent to the transverse fiber tracts of the corpus callosum.

Figure 5:
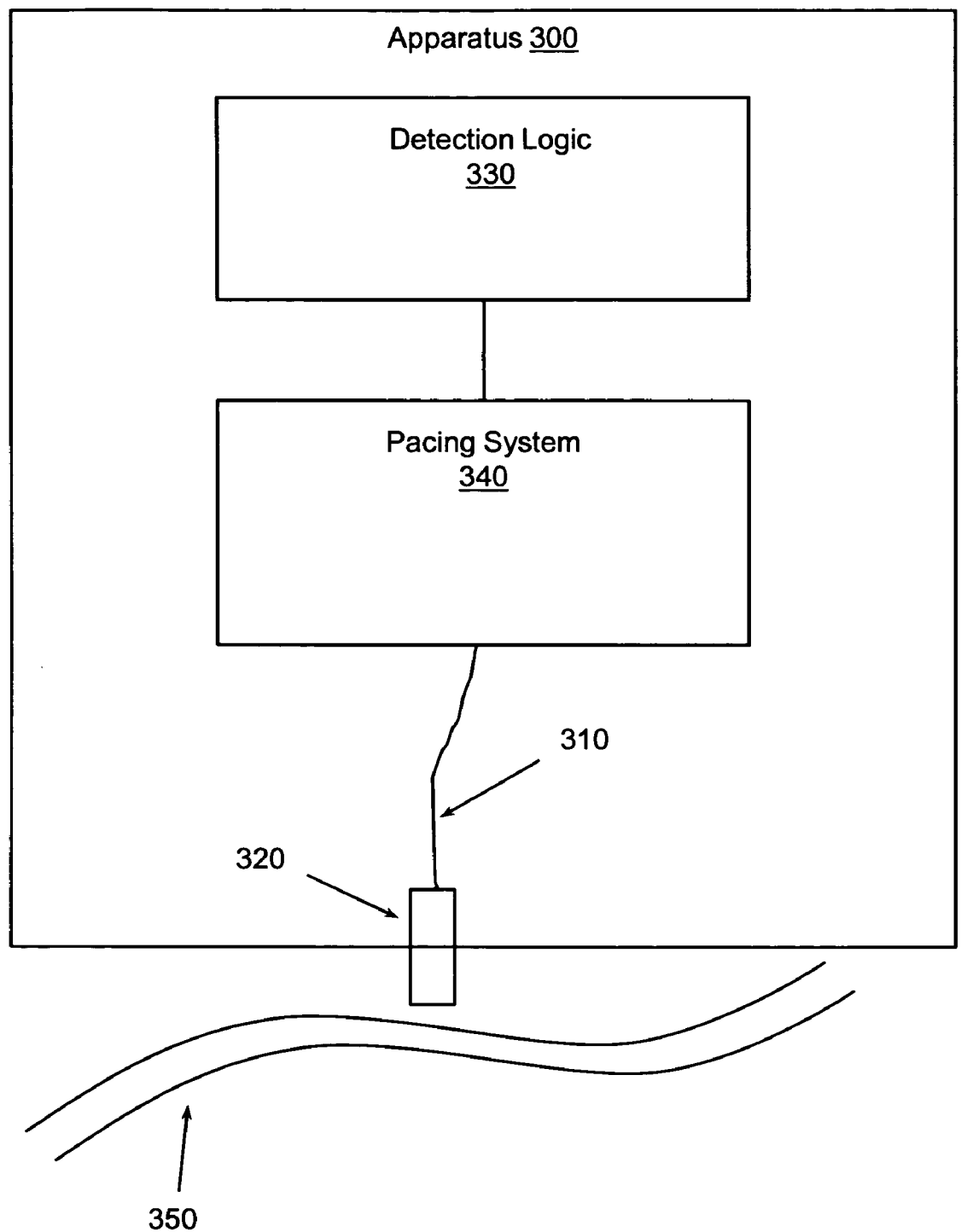
FIG. 5 illustrates an example system associated with controlling seizure activity with electrical stimulation.

FIG. 5 illustrates another embodiment of apparatus 300. This embodiment of apparatus 300 includes a detection logic 330 that detects specific electrical activity in the central nervous system of a subject. The specific electrical activity may be associated with an epileptic episode and may identify that an epileptic episode is imminent. The detection logic 330 may provide feedback to the pacing system 340 to determine the electrical stimulus to provide to alleviate the epileptic episode. The pacing system 340 and detection logic 330 may be operably connected to allow exchange of signals. In one example the stimulating electrode 320 may be used for both monitoring electrical activity and for providing the electrical stimulus. For example, the electrode could have a sensing mode that is monitored by the detection logic 330 until the pacing system 340 applies an electrical stimulus.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AAA, MB, MBB, MBBC, MBBCC, and so on (e.g., the data store may store only A, only B, only C, A&B, A&C, B&C, A&B&C, A&A&A, A&A&B, A&A&B&B, A&A&B&B&C, A&A&B&B&C&C, and so on). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A method, comprising:
controlling an implanted stimulating electrode associated with an apparatus that controls seizure activity with electrical stimulation to apply an electrical stimulus to fiber tracts of the dorsal hippocampal commissure of the brain of a human subject,
where the electrical stimulus is a high frequency electrical stimulus that suppresses propagation of epileptic episode electrical activity within fiber tracts of the hippocampal commissure, and
where the electrical stimulus is applied one of, periodically, intermittently, or continuously, before an epileptic is detected.

2. The method of claim 1, where the high frequency electrical stimulus suppresses axonal conduction between structures in the brain of a human subject.

3. The method of claim 1, where the high frequency electrical stimulus has a frequency between 80 Hertz and 300 Hertz.

4. The method of claim 1, where the high frequency electrical stimulus has a sinusoidal waveform 5. The method of claim 1, where the high frequency electrical stimulus is applied with a current in the range of one hundred micro-amps to five milli-amps.

6. The method of claim 1, where the high frequency electrical stimulus is provided as a series of pulses, where members of the series of pulses have a pulse width in the range of fifty micro-seconds to one milli-second, and where the series of pulses are applied with a current in the range of one hundre ro-amps to five milli-amps.

7. The method of claim 1, where the electrical stimulus is provided as a series of high frequency waveforms, where members of the series of high frequency waveforms are applied intermittently.

8. A method, comprising:
controlling an implanted stimulating electrode associated with an apparatus that controls seizure activity with electrical stimulation to apply an electrical stimulus to fiber tracts of the dorsal hippocampal commissure of the brain of a human subject,
where the electrical stimulus is a low frequency electrical stimulus having a frequency between 0.1 Hertz and 10 Hertz that produces a response in a target neuronal pool associated with the activation of fiber tracts of the dorsal hippocampal commissure, and
where the electrical stimulus is applied one of, periodically, intermittently, or continuously, before an epileptic episode is detected.

9. The method of claim 8, where the low frequency electrical stimulus induces an inhibitory response in the target neuronal pool.

10. The method of claim 8, where the low frequency electrical stimulus induces long-term synaptic depression in a target nucleus.

11. A method, comprising:
controlling an implanted stimulating electrode associated with an apparatus that controls seizure activity with electrical stimulation to apply an electrical stimulus to fiber tracts of the dorsal hippocampal commissure of the brain of a human subject, where the electrical stimulus includes a high frequency portion and a low frequency portion, where the high frequency portion is applied for less than seconds and selectively induces suppression of neural activity in a target nucleus, and where the low frequency portion is applied for more than ten seconds and maintains suppression of seizure activity in the target neuronal pool associated with the fiber tracts of the dorsal, hippocampal commissure, and where the electrical stimulus is applied one of, periodically, intermittently, or continuously, before an epileptic episode is detected.

12. An apparatus, comprising:

an implantable stimulating electrode adapted to provide an electrical stimulus to fiber tracts of the dorsal hippocampal commissure of the brain of a subject in which the apparatus is implanted; and a pacing system adapted to selectively apply the electrical stimulus, via the implantable stimulating electrode, to fiber tracts of the dorsal hippocampal commissure of the brain of the subject where the electrical stimulus is applied one of, periodically, intermittently, or continuously, before an epileptic episode is detected.

13. The apparatus of claim 12, where the electrical stimulus is a high frequency electrical stimulus having a sinusoidal waveform with a frequency between 80 Hertz and 300 Hertz and being delivered with a current between 100 micro-amps and 5 milli-amps, and where the high frequency electrical stimulus suppresses communication through the dorsal hippocampal commissure of signals associated with an epileptic episode in an epileptic foci.

14. The apparatus of claim 12, where the electrical stimulus is a low frequency electrical stimulus with a frequency between 0.1 Hertz and 10 Hertz that produces a response in a target neuronal pool associated with the fiber tracts of the dorsal hippocampal commissure, the response being one of, a synchronization in the target neuronal pool, and an inhibitory response in the target neuronal pool.

* * * * *